United States Patent
Mann

(10) Patent No.: US 8,272,737 B2
(45) Date of Patent: Sep. 25, 2012

(54) WIDE-ANGLE OBSERVATION AT A SURGICAL MICROSCOPE

(75) Inventor: Dieter Mann, Kleinwallstadt (DE)

(73) Assignee: Dieter Mann GmbH, Mainaschaff (DE)

( * ) Notice: Subject to any disclaimer, the term of this patent is extended or adjusted under 35 U.S.C. 154(b) by 195 days.

(21) Appl. No.: 12/565,588

(22) Filed: Sep. 23, 2009

(65) Prior Publication Data

US 2010/0265460 A1 Oct. 21, 2010

Related U.S. Application Data

(60) Provisional application No. 61/170,975, filed on Apr. 20, 2009.

(30) Foreign Application Priority Data

Apr. 20, 2009 (DE) .......................... 10 2009 018 114

(51) Int. Cl.
*A61B 3/10* (2006.01)
*A61B 18/18* (2006.01)

(52) U.S. Cl. ............ 351/205; 351/214; 351/221; 606/4; 606/5; 606/6

(58) Field of Classification Search .................. 351/205, 351/214, 221; 250/310, 311; 359/385, 659
See application file for complete search history.

(56) References Cited

U.S. PATENT DOCUMENTS

| | | | |
|---|---|---|---|
| 2,622,473 A | 12/1952 | Littman | |
| 5,793,524 A | 8/1998 | Luloh | |
| 6,788,455 B2 | 9/2004 | Kirchhuebel et al. | |
| 7,011,410 B2 * | 3/2006 | Bolger et al. | 351/209 |
| 2002/0044256 A1 | 4/2002 | Kirchhuebel | |
| 2002/0191280 A1 | 12/2002 | Horiguchi et al. | |
| 2004/0184143 A1 * | 9/2004 | Akiyama et al. | 359/381 |
| 2005/0225848 A1 | 10/2005 | Kirchhuebel | |
| 2006/0232856 A1 | 10/2006 | Horiguchi et al. | |
| 2008/0204660 A1 | 8/2008 | Obrebski | |
| 2009/0219483 A1 | 9/2009 | Takanashi et al. | |

FOREIGN PATENT DOCUMENTS

| | | |
|---|---|---|
| DE | 814 798 C | 9/1951 |
| DE | 102 26 874 A1 | 6/2002 |
| DE | 10336893 | 5/2004 |
| DE | 60 2004 006 178 T2 | 12/2007 |
| DE | 60 2004 005 764 T2 | 1/2008 |
| EP | 1199591 A1 | 4/2002 |
| EP | 1227355 B1 | 7/2002 |
| EP | 1 450 194 A2 | 8/2004 |
| EP | 1 679 540 A1 | 7/2006 |
| EP | 1 447 698 B1 | 4/2007 |
| EP | 1 450 193 B1 | 5/2007 |
| EP | 1 889 567 A2 | 2/2008 |
| EP | 2 096 481 A2 | 9/2009 |

* cited by examiner

*Primary Examiner* — Ricky Mack
*Assistant Examiner* — Mahidere Sahle
(74) *Attorney, Agent, or Firm* — McDonnell Boehnen Hulbert & Berghoff LLP

(57) ABSTRACT

A microscope for performing an opthalmo-surgical intervention, in particular for a contactless wide-angle observation of an eye during an intervention, is provided. The microscope has a tube (1a) having an objective and an ocular, a holding arm (1), at which the tube (1a) is attached such that a movement of the objective with respect to the holding arm (1) along the optical axis of the objective is possible, an optical accessory part (8a) between the objective and the eye and a holding device for the optical accessory part (8a). The holding device for the optical accessory part is attached at the holding arm (1) by means of an attachment device (2) in such a way that the holding device does not take part in movements of the objective along the optical axis of the objective. Thereby, when changing the picture angle, a re-adjustment is highly simplified.

15 Claims, 7 Drawing Sheets

WIDE-ANGLE OBSERVATION AT A SURGICAL MICROSCOPE

The invention is related to a microscope that allows a contactless wide-angle observation during an opthalmo-surgical intervention or that allows an intervention with the aid of a contact glass that has been put onto the eye. In particular, the invention refers to a surgical microscope that can be used in an opthalmo-surgical intervention, which surgical microscope allows observation of the fundus (eyeground) at least intermittently.

For operations in the rear section of the eye in particular a wide-angle observation is required. In the prior art it is known to make a wide-angle observation by placing a lens between the objective of the microscope and the eye. For instance, a contact lens or a contact glass can be put onto the eye. However, the disadvantage of using such a contact lens is that the picture angle is limited to 68° at maximum.

Figure 5:
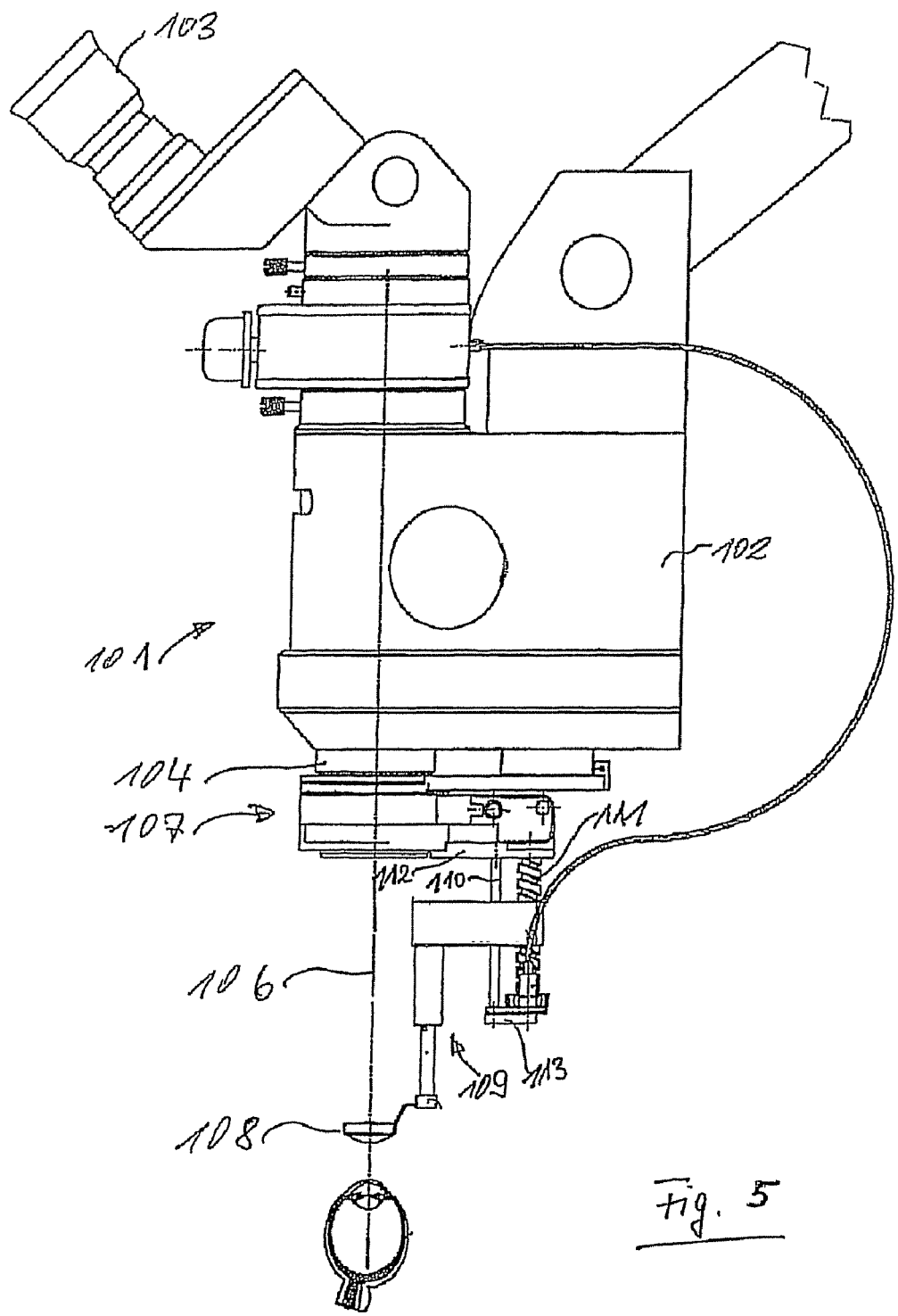

In order to avoid this disadvantage EP 1 199 591 A1 suggests to provide between the objective and the eye an optics that is adjustable by an electric motor and which does not have immediate contact to the eye. In this optics a drive by means of an electric motor allows a re-focussing, so that the surgeon does not need to discontinue the intervention. FIG. 5 shows the corresponding arrangement.

In FIG. 5 a microscope 101 has a housing 102 with an eyepiece 103 and an objective 104. A mounting 107 is mounted on the lens, which mounting is non-movable relative to the objective 104 in the direction of the optical axis 106 and serves for fixing a front optics 108 to the objective 104. The optics 108 consists of a front lens that is attached at a holding arm 109, which holding arm 109 is movable in direction of the optical axis 106. Here, a stationary rod 110 and a threaded spindle 111 are attached to the mounting 107, which rod 110 and threaded spindle 111 extend parallel to the optical axis. The stationary rod 110 and the threaded spindle 111 on the one side are supported on a base plate 112 of the mounting 107, which base plate 112 is mounted at the objective, and on the other side are supported at a bridge 113.

The arrangement is designed in such a way that the front optics 108 can be swung into the beam path 106 of the microscope 101 and can be swung again out of this position. This surgical microscope according to the prior art is considered to have the disadvantage that the focussing is difficult after the auxiliary optics has been swivelled into the beam path or swivelled out of it. For instance, when the front lens 108 is brought into the beam path, for a focussing not only the distance between the lens 108 and the objective 104 has to be changed, but in addition also the distance between the objective 104 and the eye has to be changed. Although the corresponding lenses can be moved by a pedal switch by means of an electric motor, so that the surgeon need not loose his hold of the instruments that are located in the eye, the focussing is cumbersome because the position of two lenses has to be changed, which lenses are not independent from one another when controlling the focus.

In addition, when a lens is swivelled into the beam path, there is still the problem that a right-left reversed upside down image is generated, which image disturbs the surgeon due to the direction of movement of the instruments in the eye opposite to the movement direction of the hand. In EP 1 227 355 B1 it is proposed to swivel an image reversal device into the beam path and out of the beam path together with the front lens, however the problem of a complicated focussing still remains:

As the distance between the front lens and the eye changes in EP 1 199 591 A1 each time when the focus is modified, an independent adjustment of the front lens is necessary.

Figure 6:
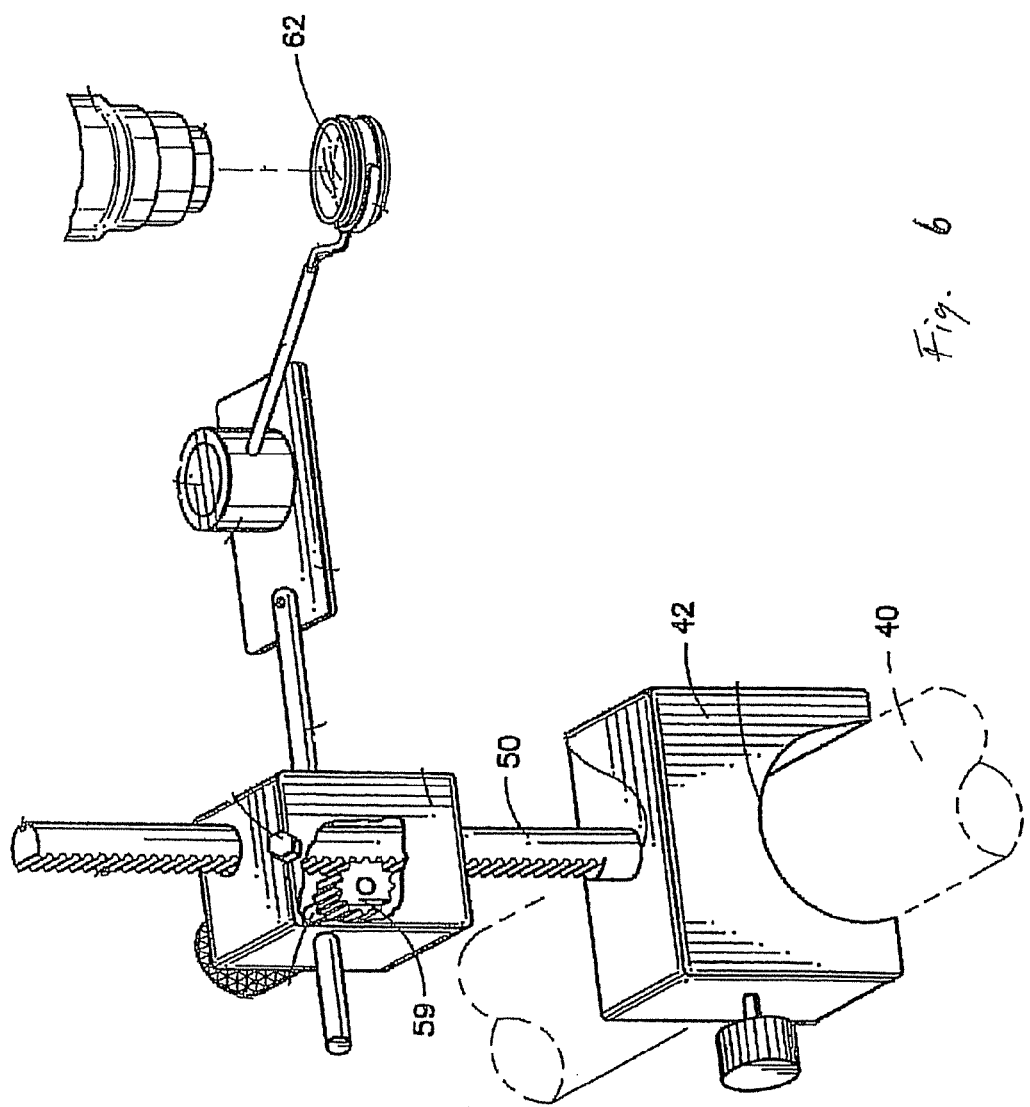

Therefore, in U.S. Pat. No. 5,793,524 it is proposed to fix the distance between the front lens and the patient's eye. For this purpose the front lens is located at a ring-shaped mounting that is surrounding the patient's head, which mounting is fastened at the surgery table on which the patient is lying. FIG. 6 shows such a mounting having the front lens 62. The lens can be adjusted in height by means of a rack and pinion device 50, 59. In FIG. 6 also a support block 42 is shown, which has a cylindrical recess for a fixation at a cylindrical wrist rest 40 for the surgeon as it is usually used in the United States.

The disadvantage of this device is that for example outside of the United States it is rather unusual to provide a wrist rest at the surgery table. Thus, the device makes it necessary to have a specially designed surgery table. A further disadvantage is that when the patient's eye moves, on the one hand the position of the front lens has to be corrected and on the other hand the adjustment of the microscope to the patient's eye and to the front lens has to be corrected. In such a case an interruption of the surgical intervention is nearly unavoidable.

Similarly, also when using a contact glass that has to be put onto the eye, it is necessary to discontinue the intervention if no second person is assisting who will hold the contact glass in position.

In view of the above described disadvantages of the prior art it is an object of the invention to provide a microscope that allows during a surgical intervention at the eye a simple positioning of an optical accessory part.

The object is achieved by a microscope according to claim 1.

Further developments according to the invention are specified in the dependent claims.

Figure 1A:
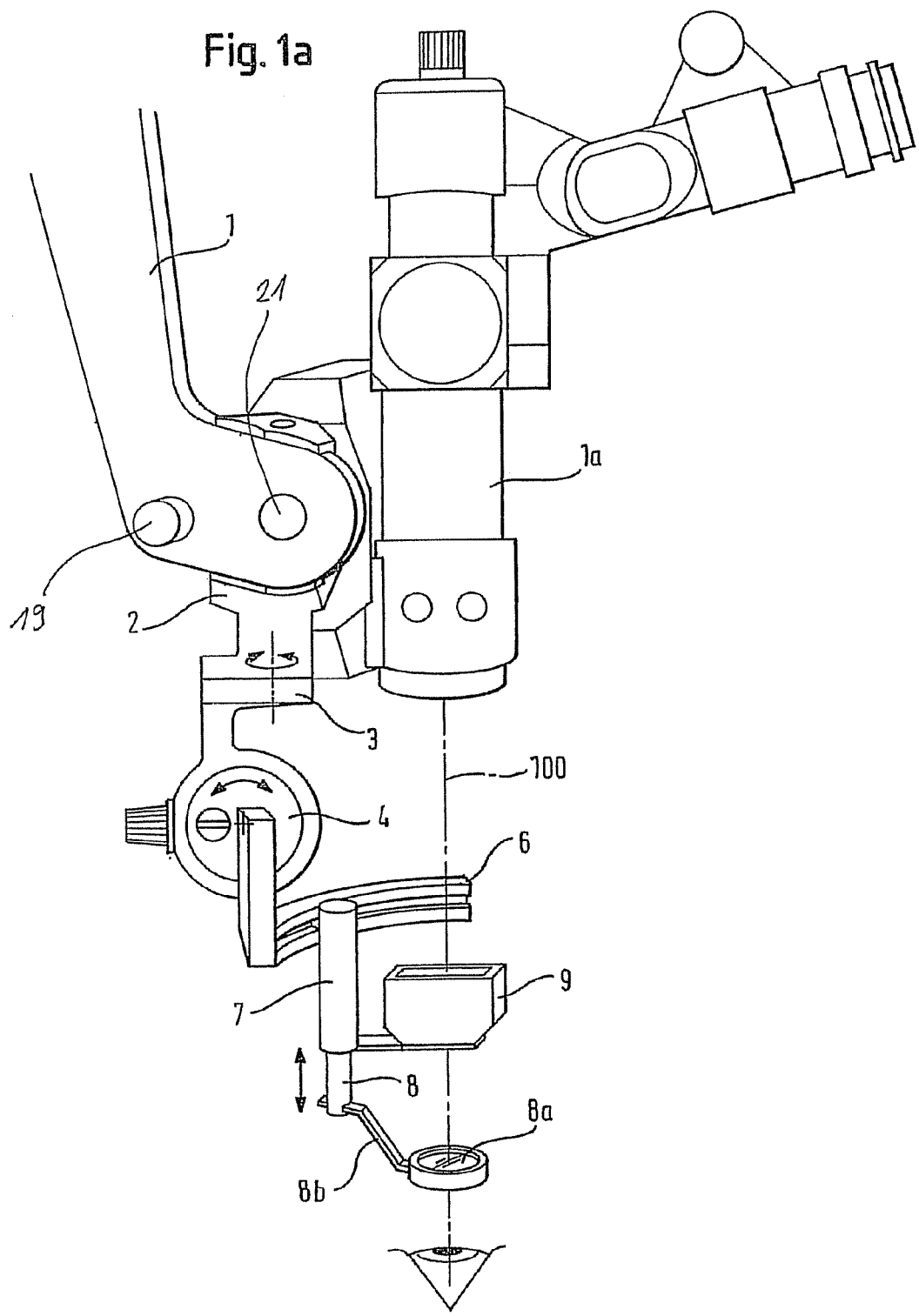
Figure 1B:
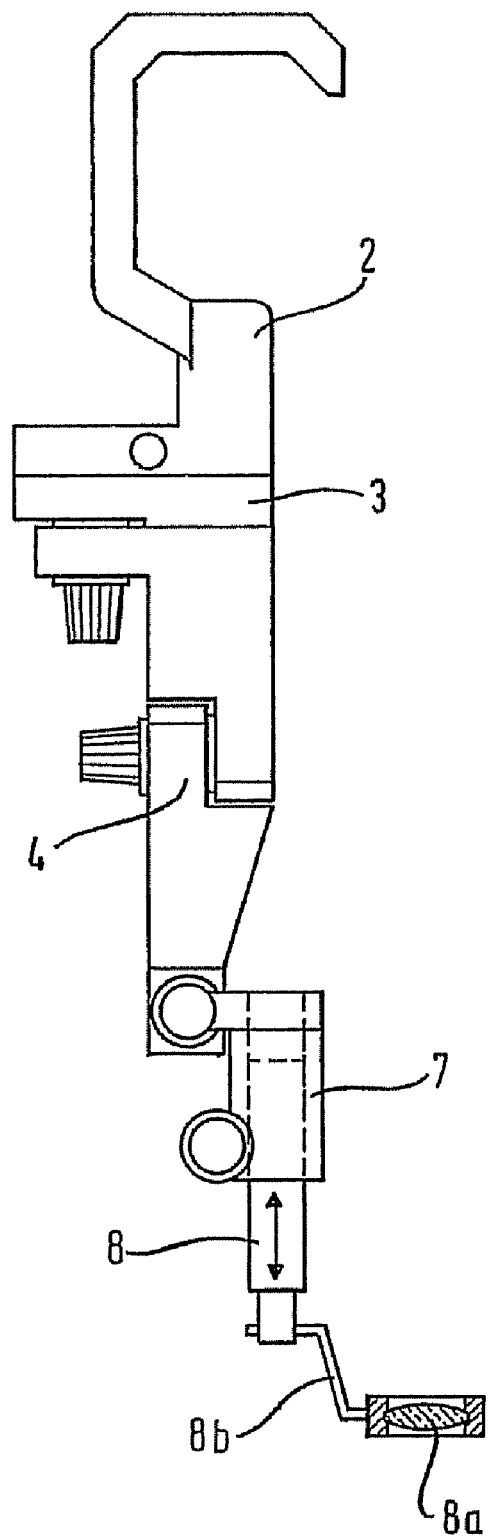
Figure 2:
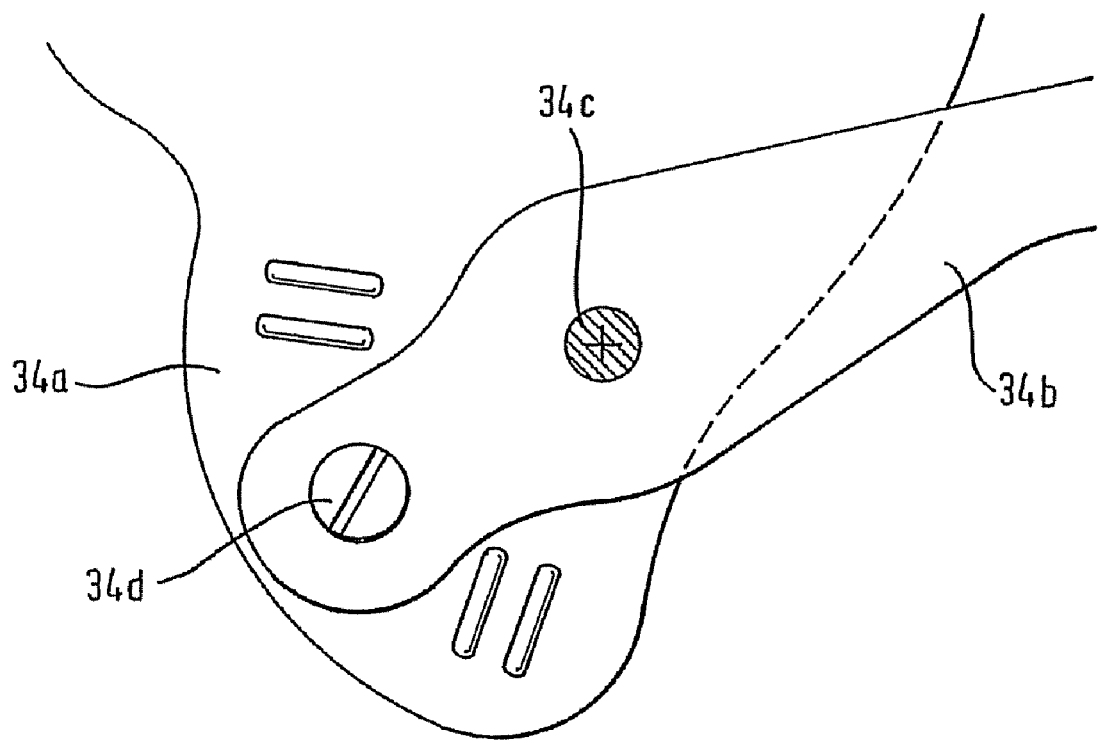
Figure 3:
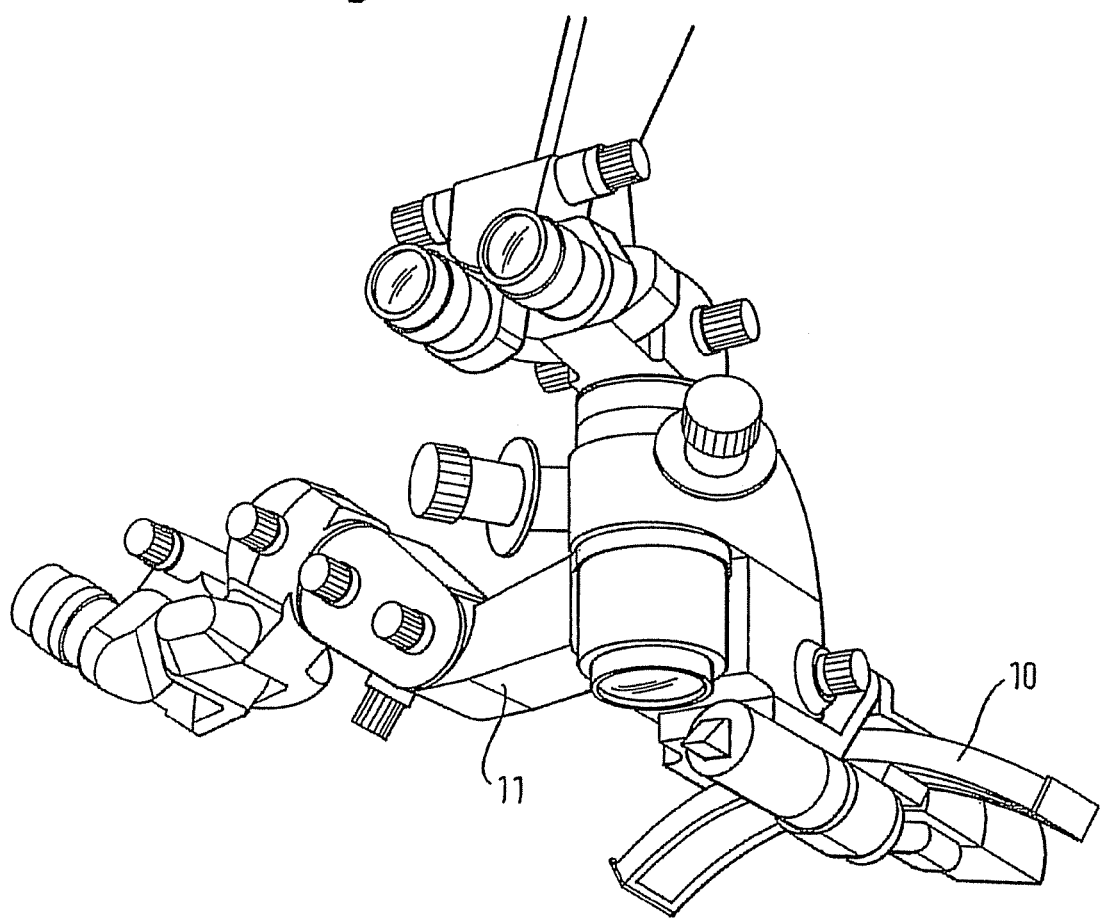
Figure 4:
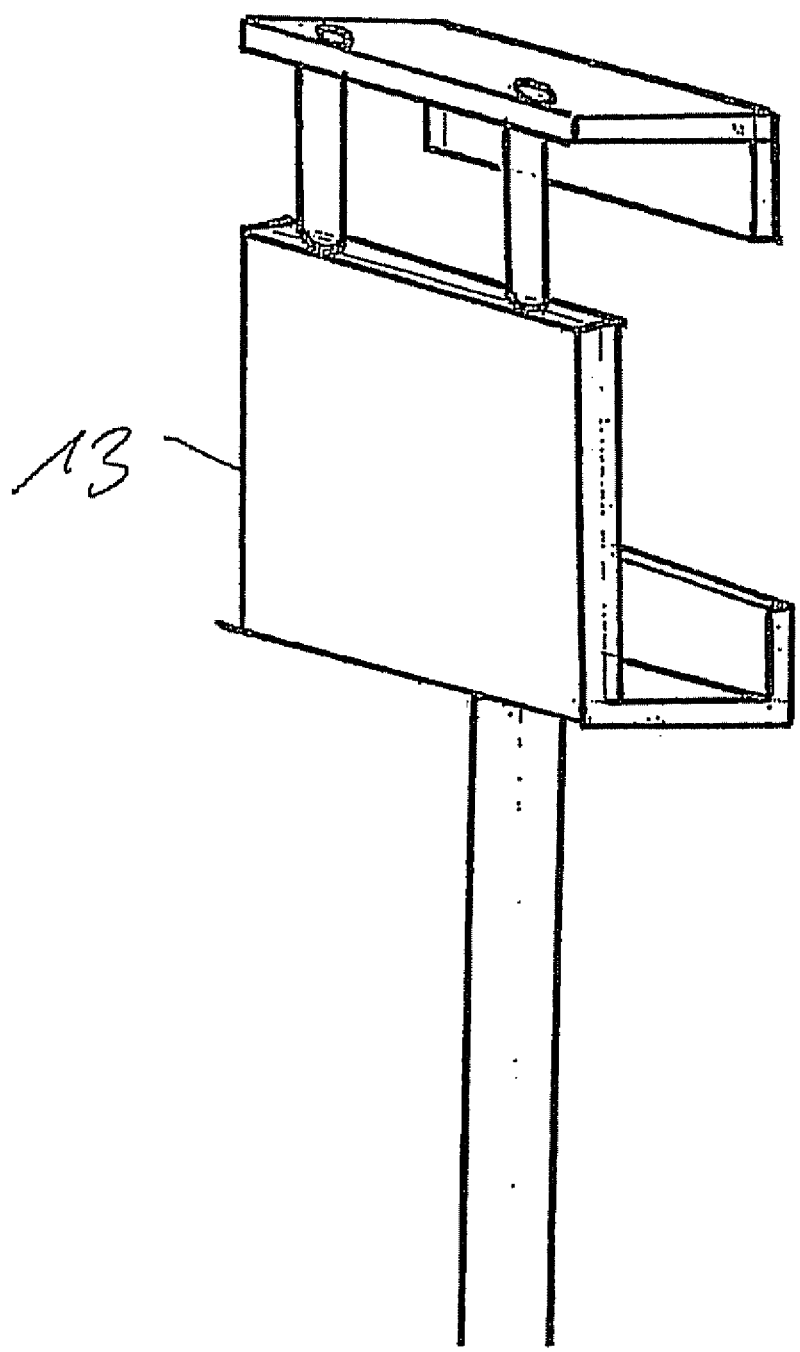

Further features and advantages of the invention arise from the description of embodiments based on the attached figures, of which:

FIG. 1a shows the overall setup of a surgery microscope according to the invention, in which a front lens for a wide-angle observation has been inserted into the beam path, FIG. 1b shows a side view of a holding device for the front lens, FIG. 2 shows the construction of a swivelling device, FIG. 3 shows the surgical microscope according to the invention combined with a co-observation microscope and a slit lamp, FIG. 4 shows an alternative possibility of attaching the holding device for the front lens at the holding arm of the surgical microscope, FIG. 5 shows the overall setup of a surgical microscope including a front lens according to the prior art, and FIG. 6 shows a further possibility for an attachment of a front lens according to the prior art.

FIRST EMBODIMENT

FIG. 1a shows an embodiment of the surgical microscope having a front lens for a wide-angle observation. A tube 1a with an objective and an ocular attached to it is attached to a holding arm 1 for the microscope in such a way that a movement of the whole tube 1a or at least a movement of the objective with respect to the holding arm 1 along the optical axis of the objective is possible. An attachment device 2 for affixing a holding device for the front lens on the holding arm 1 is provided at the holding arm. FIG. 1b shows a side view of the holding device for the front lens. There, the attachment device 2 is exemplified as a hook. The holding device consists of a first swivelling device 4 for swivelling around a first axis such as a horizontal axis, a second swivelling device 3 for swivelling around an axis that is parallel to the optical axis of the objective, a semi-circular support 6 for rotating a front lens 8a around an axis that is perpendicular to the lens plane, an optional image reversal device 9 and the actual lens holder 7, 8.

In FIGS. 1a and 1b the second swivelling device 3 is arranged closer to the holding arm 1 than the other parts of the holding device. However, it would also be possible to exchange in the figure the positions of the first and second swivelling devices.

In particular, it would also be possible to design the first swivelling device 4 such that it serves simultaneously as attachment device 2 for affixing the holding device for the front lens at the holding arm 1. In this case one of the two parts to be swivelled against each other would be rigidly connected to the holding arm 1, for example by means of a screw coupling.

The setup of the swivelling devices 3 and 4 is exemplified in FIG. 2. Each one of the first and second swivelling devices consists substantially of two parts 34a and 34b that are connected with each other via a bolt 34c such that they can be rotated against each other. Here, the locking of the relative positions of the two parts 34a and 34b that can be swivelled against each other is effected by means of a locking device 34d. For instance, such a locking device can be designed as locking screw, which is screwed into a screw hole formed in one swivelling part 34b. The end opposite to the screw head may e.g. be semi-spherically shaped.

Here, advantageously a recess is formed in the other swivelling part 34a, with which recess the screw end engages. In order to form the recess, the swivelling part 34a may be worked off at certain positions. Alternatively, elevations may be formed in the swivelling part 34a, between which elevations the semi-spherical screw end may be lowered. In FIG. 2 the elevations are for example parallel steel rods, wherein one half of each rod is sunk into the other part 34a.

The screw head of the locking screw 34d need not necessarily be semi-spherical, but may be formed also in an arbitrary shape. Furthermore, in FIG. 2 the locking device is only exemplarily shown to have a lever. Other designs of the head of the locking screw (locking device) are also possible. In particular, it is possible to provide a sterilizable cap at the screw head.

The semi-circular support 6 is designed as guide rail, on which guide rail a lens support receptacle 7 being a part of the actual lens holder may slide along. Here, it does not matter how the guide rail is shaped. In particular, for moving the lens support receptacle 7 on the semi-circular support 6 a protrusion of the lens support receptacle 7 may engage with a recess on the semi-circular support 6 or else a protrusion on the semi-circular support 6 engages with a recess of the lens support receptacle 7.

The actual lens support 8, which in the figure is rod-shaped or cylindrical, can be moved vertically, which means in the direction of the cylinder axis for the case that it is cylindrical, such that it enters a recess, which is e.g. cylindrical, at the bottom end of the lens support receptacle 7.

Thereby the lens support 8 may be vertically adjusted by lifting it. In particular, there is no locking in a lifted position. Furthermore, no large resistance has to be overcome for lifting the front lens together with the lens support due to the sliding of the upper end of the lens support 8 in the bottom end of the lens support receptacle 7. Thereby a damage to the patient's eye for an incorrect positioning of the surgical microscope is prevented.

The front lens 8a is mounted in a ring, which is connected to the lens support 8 via a support bar 8b. For instance, the support bar 8b engages with the horizontal slit at the lower end of the lens support 8.

An adjustment of the front lens 8a in order to bring it into the beam path 100 is effected within a plane that is perpendicular to the optical axis of the objective by swivelling the holding device for the front lens 4, 6, 7, 8, 8b with respect to the holding arm 1 by means of the second swivelling device 3. By moving the lens support receptacle 7 in the guide rail of the semi-circular support 6, the lens support receptacle 7, the lens support 8, the support bar 8b and the front lens 8a can additionally be rotated with respect to the axis 100 of the beam path. This is necessary for adjusting the semi-circular support 6, the lens support receptacle 7 and the lens support 8 relative to the lid gap (palpebral fissure). Such an adjustment possibility is necessary for example when switching from one eye to the other eye or else for avoiding a contact with a lid retractor.

When the front lens 8a is not needed, it can be swivelled to the side together with the semi-circular guide rail 6, the lens support receptacle 7, the lens support 8 and the support bar 8b by means of the first swivelling device 4.

In the previously described device the front lens via its holder is attached to the holding arm 1 of the microscope, so that it does not take part in the position change of the tube 1a along the axis of the observation beam path, but rests in the preset position with respect to the eye. Thereby the focussing is simplified, because only the microscope tube 1a has to be vertically moved when an adjustment for obtaining a sharp image has to be made.

Furthermore, the attachment of the front lens holder at the holding arm of the microscope allows a fixed adjustment of the position of the front lens 8a in a plane that is perpendicular to the observation beam path 100 or perpendicular to the optical axis of the objective. Thereby, when the patient moves, the retrieval of the surgical region is made easier. The front lens and the microscope need not be adjusted independently from each other to the new position of the patient. Rather, both can be commonly adjusted by re-adjusting the microscope as a whole.

As the image is turned upside down and is reversed left to right, when the front lens 8a is swivelled into the beam path of the microscope, it is necessary to rotate the image by 180° by inserting an image reversal device such as a Schmidt prism. As is shown in FIG. 1, such an image reversal device 9 may for example be attached at the lens support receptacle 7, so that it may be swivelled into the beam path together with the front lens 8a. Alternatively, such an image reversal device may also be attached at the tube 1a and may be moved into the beam path by the operation of a pedal switch. An attachment at the tube has the disadvantage that due to the overall height of the image reversal device such an attachment leads to an increase of the overall height of the microscope and thus leads to a higher eyepiece position with respect to the patient's eye. Some operators may find the increased distance to the eye, which is caused thereby, to be disadvantageous.

According to the invention a holding device for the front lens is not attached at the objective. Therefore, there is space for additional instruments in the area of the objective. FIG. 3, which out of reasons of a better illustration does not show the holding device according to the invention, shows a co-observation microscope 11 as well as a slit lamp 10 as examples for additional instruments. Due to the free space around the objective the change of the positioning of the co-observation microscope 11 from the right eye to the left eye of the patient and vice versa is not obstructed. Furthermore, there is also sufficient space for the attachment of a motor-driven slit lamp 10. The common use of the wide-angle front lens 8a together with a fibre slit lamp 10 has a particular advantage when examining small children (premature infants).

The attachment device 2 for attaching the front lens holder (3, 4, 6, 7, 8, 8a, 8b) at the holding arm 1 of the microscope can be implemented in different ways. For instance, it can be implemented by means of a dove tail guide or else can consist of the hook 2 shown in FIG. 1b, which hook is attached at the connection axis 3 of the microscope holding arm 1 and the microscope.

FIG. 4 shows still another possibility of an attachment, wherein a shoe 13 is formed at the holding device for the front lens, which shoe 13 encompasses the holding arm 1.

It is particularly advantageous to mount the attachment device 2 on the holding arm 1 in such a way that it can be tilted with respect to the holding arm 1. FIG. 1a illustrates this by showing a tilt axis 21, around which the front lens holder (3, 4, 6, 7, 8, 8a, 8b) together with the microscope, including the tube 1a, can be tilted. The tilt is set by means of the operating knob 19 that is shown.

It has to be pointed out that the tube 1a and the attachment device 2 can be tilted conjointly with respect to the holding arm 1, though the tube 1a is movable in height with respect to the attachment device 2. Due to this a re-adjustment of the surgery microscope while maintaining the distance between the front lens and the objective is significantly simplified in the case of movements of the patient: A still further degree of freedom for a movement of the surgery microscope is provided.

Of course, the above-described tilting possibility can also be effected by means of the first swivelling device 4, which in such a case at the same time serves as attachment device 2 for an attachment at the holding arm 1 as it was already described above.

Though previously always a front lens was mentioned, the invention of course is also applicable to differently designed front optics such as lens systems.

It is possible to provide a first fine adjustment device for a fine adjustment of the front lens 8a on the optical axis of the objective.

Furthermore, it is possible to provide an additional second fine adjustment device such as a cross table for a fine adjustment of the position of the front lens 8a in a plane perpendicular to the optical axis of the objective.

The first and second fine adjustment devices may for example be implemented by providing an eccentric screw at each of the first and second swivelling devices 3, 4, which eccentric screw engages with the recess, with which also the locking device 34d engages. A fine adjustment is then possible by a slight turning of the eccentric screw.

Preferably all components of the front lens holder except the image reversal device 9 and the attachment device 2 should be autoclavable.

Second Embodiment

A second embodiment of the invention differs from the first embodiment only by the feature that the front lens mentioned in the first embodiment is now a lens to be put onto the cornea of the eye or a contact glass 8a' to be put onto the cornea of the eye, which contact glass 8a' may contain several lenses. Such a lens and such a contact glass, respectively, in the following to simplify matters and without intending to limit the invention thereto only a contact glass is mentioned, are also mounted at the holding arm 1 of the microscope via the front lens holder 3, 4, 6, 7, 8, 8b and the attachment device 2. A contact glass, which is held like this, is operated as follows:

In the course of a surgical intervention the contact glass can be swivelled into the observation beam path of the microscope by means of the first swivelling device 4 and/or the second swivelling device 3. Here, of course, an injury of the eye has to be avoided. In this regard a free vertical movement of the lens support 8 in the lens support receptacle 7, as it was described in the first embodiment, is advantageous.

In order to put the contact glass onto the eye at first the lens support 8 is moved to its highest position in the lens support receptacle 7. In this position the contact glass 8a' is mounted on the lens support 8, e.g. by means of a retainer and a support bar 8b. After this the contact glass 8a' is swivelled into the observation beam path and the lens support 8, the support bar 8b and the contact glass 8a' are lowered with caution. At the end the self-weight of the contact glass, the weight of the retainer, the weight of the support bar, which is eventually present, and the weight of the lens support together rest on the eye, on which advantageously there was applied before a sterile contact gel.

In a modification of the present embodiment a facility for arresting the lens-support 8 in its upper-most position in the lens support receptacle 7, thus the position in which the lens support has the largest distance to the patient's eye, may be provided. Here, the arrest can be made for example by means of a magnetic contact between the lens support and the bottom of the recess at the lower end of the lens support receptacle 7. Thereby the lens support 8 need not be actively held in its uppermost position during the mounting of the contact glass 8a' on the lens support 8, so that the course of movements is simpler for the operator. As soon as the contact glass 8a' is located in the observation beam path, the arrest of the lens support is released, so that the contact glass may move down onto the patient's eye.

In a magnetic arrest the arrest could e.g. be activated and released by means of a electromagnet. However, of course also mechanical means such as detents are feasible for implementing an arrest. These mechanical means can be used in addition to a magnetic contact or instead of a magnetic contact.

Thus, by the invention it is possible to put the contact glass onto the eye in a controlled way and to lock it horizontally in such a position. Due to the simple and well controllable handling the swivelling of the contact glass into the observation beam path and the height adjustment of the contact glass can be done by the operator (surgeon) himself. The support by an assistant is not necessary. In particular the fact that the lens support 8 is able to move freely in the lens support receptacle 7 allows the operator to move the eye relative to the contact glass in a state where the contact glass sits on the eye.

In other respects all modifications and arrangements that were described in conjunction with the first embodiment are equally applicable to the second embodiment.

Though in the above description only front lenses, front lens systems or contact glasses were mentioned, it is of course possible to attach any optical part at the holding arm 1 of the microscope by means of the described front lens holder 3, 4, 6, 7, 8, 8b and the described attachment device 2. Therefore, in the following claims in general an "optical accessory part" or "optical front part" is mentioned.

The invention claimed is:

1. A surgical microscope for an opthalmo-surgical intervention having: a tube having an objective and an ocular, a microscope holding arm, at which the tube is fastened such that a movement of the objective against the microscope holding arm along the optical axis of the objective is possible, an optical accessory part between the objective and the eye and a holding device for the optical accessory part, said optical accessory part including a lens having a lens plane, an attachment device, by means of which the holding device for the optical accessory part is fixed at the microscope holding arm, and a rotation device for rotating said lens around an axis that is perpendicular to said lens plane, wherein said rotation device includes a guide rail and a support receptacle for the optical accessory part, and wherein said support receptacle is configured to slide along said guide rail, and wherein said guide rail is positioned in an arcuate manner around the optical axis of the objective.

2. The microscope according to claim 1, which furthermore comprises a first swivelling device for swivelling the optical accessory part around an axis.

3. The microscope according to claim 2, in which the attachment device is mounted on the microscope holding arm such that the attachment device can be tilted relative to the microscope holding arm around an axis together with the tube and the holding device for the optical accessory part.

4. The microscope according to claim 2, in which the first swivelling device is arranged such that a common swivelling of the rotation device and the optical accessory part is possible.

5. The microscope according to claim 2, which furthermore comprises a second swivelling device for swivelling the optical accessory part around an axis that is parallel to the optical axis of the objective.

6. The microscope according to claim 5, in which the second swivelling device is arranged such that a common swivelling of the first swivelling device, the rotation device and the optical accessory part is possible.

7. The microscope according to claim 1, which further comprises an image reversal device that is arranged between the objective and the optical accessory part.

8. The microscope according to claim 7, in which a first swivelling device is arranged such that by means of the first swivelling device a common swivelling of the image reversal device and the optical accessory part is possible.

9. The microscope according to claim 8, in which a second swivelling device is arranged such that by means of the second swivelling device a common swivelling of the image reversal device and the optical accessory part is possible.

10. The microscope according to claim 2, in which the first swivelling device at the same time serves as attachment device for attaching the holding device for the optical accessory part at the microscope holding arm.

11. The microscope according to claim 1, further comprising a fibre slit lamp so that an illumination with the fibre slit lamp through the optical accessory part is possible.

12. The microscope according to claim 1, wherein said optical accessory part is a lens or a lens system, such that a contactless wide-angle observation of a fundus is made possible.

13. The microscope according to claim 1, wherein said optical accessory part is a contact glass, which is adapted to be put onto an eye.

14. The microscope according to claim 1, further comprising
   a lens support and
   a lens support receptacle,
wherein
   said optical accessory part is mounted on said lens support,
   said lens support is arranged in said lens support receptacle such that said lens support protrudes from a bottom of said lens support receptacle,
   said lens support receptacle is a component of the holding device for the optical accessory part and
   said lens support is able to move freely, which means without any resistance that is impeding the movement, in the lens support receptacle.

15. The microscope according to claim 2, in which the axis, around which there is a swivelling, is a horizontal axis.

* * * * *